US 8,444,602 B2

(12) United States Patent
Valaie

(10) Patent No.: US 8,444,602 B2
(45) Date of Patent: May 21, 2013

(54) HEMOSTATIC VALVE SYSTEM

(75) Inventor: Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1628 days.

(21) Appl. No.: 11/223,333

(22) Filed: Sep. 9, 2005

(65) Prior Publication Data
US 2007/0078395 A1    Apr. 5, 2007

(51) Int. Cl.
*A61M 5/178*    (2006.01)
*A61M 5/00*    (2006.01)

(52) U.S. Cl.
USPC ............ 604/167.03; 604/164.01; 604/167.01; 604/246

(58) Field of Classification Search
USPC ................ 604/164.01, 93.01, 48, 27, 167.03, 604/256, 167.01, 167.02, 167.04, 167.06, 604/246, 264, 158, 164.02
See application file for complete search history.

(56) References Cited

U.S. PATENT DOCUMENTS

| | | | |
|---|---|---|---|
| 2,321,336 A | 6/1943 | Tondreau |
| 2,416,391 A | 2/1947 | Hixson |
| 2,844,351 A | 7/1958 | Smith |
| 3,185,179 A | 5/1965 | Harautuneian |
| 3,304,934 A | 2/1967 | Bautista |
| 3,329,390 A | 7/1967 | Hulsey |
| 3,599,637 A | 8/1971 | Schwartz |
| 4,000,739 A | 1/1977 | Stevens |
| 4,016,879 A | 4/1977 | Mellor |
| 4,063,555 A | 12/1977 | Ulinder |
| 4,243,034 A | 1/1981 | Brandt |
| 4,311,137 A | 1/1982 | Gerard |
| 4,314,555 A | 2/1982 | Sagae |
| 4,424,833 A | 1/1984 | Spector et al. |
| 4,540,411 A | 9/1985 | Bodicky |
| 4,580,573 A | 4/1986 | Quinn |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,798,594 A | 1/1989 | Hillstead |
| 4,895,565 A | 1/1990 | Hillstead |

(Continued)

FOREIGN PATENT DOCUMENTS

| | | |
|---|---|---|
| EP | 0 344 907 B1 | 12/1989 |
| EP | 0 550 069 A1 | 7/1993 |

(Continued)

*Primary Examiner* — Kevin C Sirmons
*Assistant Examiner* — Shefali Patel
(74) *Attorney, Agent, or Firm* — Brinks Hofer Gilson & Lione

(57) ABSTRACT

A medical introducer apparatus for use in inserting an interventional device into a body vessel of a patient. The apparatus includes a housing having a proximal opening, a distal opening, and a chamber positioned between the proximal and distal openings. A sheath, defining a conduit for the interventional device, extends distally from the housing distal opening. A hemostatic valve system is provided in the housing chamber. The valve system includes a plurality of generally elastomeric valve members axially arranged in the chamber. The valve members each have a generally circular hole extending therethrough, which hole is sized for substantially leak-free passage of the interventional device. The valve members are aligned in the chamber to be sequentially penetrable by the interventional device, such that the hole in one valve member is covered by an adjoining valve member.

13 Claims, 5 Drawing Sheets

U.S. PATENT DOCUMENTS

| | | | |
|---|---|---|---|
| 4,929,235 A | | 5/1990 | Merry et al. |
| 4,932,633 A | | 6/1990 | Johnson et al. |
| 4,978,341 A | | 12/1990 | Niederhauser |
| 5,000,745 A | * | 3/1991 | Guest et al. .................. 604/256 |
| 5,006,113 A | | 4/1991 | Fischer |
| 5,009,391 A | | 4/1991 | Steigerwald |
| 5,053,013 A | | 10/1991 | Ensminger et al. |
| 5,066,285 A | | 11/1991 | Hillstead |
| 5,102,395 A | | 4/1992 | Cheer et al. |
| 5,125,903 A | | 6/1992 | McLaughlin et al. |
| 5,154,701 A | | 10/1992 | Cheer et al. |
| 5,158,553 A | | 10/1992 | Berry et al. |
| 5,167,637 A | * | 12/1992 | Okada et al. ............ 604/167.04 |
| 5,176,652 A | * | 1/1993 | Littrell ...................... 604/167.04 |
| 5,211,370 A | | 5/1993 | Powers |
| 5,242,413 A | | 9/1993 | Heiliger |
| 5,256,150 A | | 10/1993 | Quiachon et al. |
| 5,267,966 A | | 12/1993 | Paul |
| 5,304,156 A | | 4/1994 | Sylvanowicz et al. |
| 5,350,363 A | | 9/1994 | Goode et al. |
| 5,350,364 A | | 9/1994 | Stephens et al. |
| 5,376,077 A | | 12/1994 | Gomringer |
| 5,385,552 A | * | 1/1995 | Haber et al. ............. 604/167.03 |
| 5,395,349 A | | 3/1995 | Quiachon et al. |
| 5,395,352 A | | 3/1995 | Penny |
| 5,409,463 A | | 4/1995 | Thomas et al. |
| 5,484,418 A | | 1/1996 | Quiachon et al. |
| 5,538,505 A | | 7/1996 | Weinstein et al. |
| 5,613,956 A | | 3/1997 | Patterson et al. |
| 5,643,227 A | | 7/1997 | Stevens |
| 5,653,697 A | | 8/1997 | Quiachon et al. |
| 5,702,370 A | | 12/1997 | Sylvanowicz et al. |
| 5,779,681 A | | 7/1998 | Bonn |
| 5,895,376 A | | 4/1999 | Schwartz et al. |
| 5,935,122 A | | 8/1999 | Fourkas et al. |
| 6,086,570 A | * | 7/2000 | Aboul-Hosn et al. ........ 604/256 |
| 6,197,016 B1 | | 3/2001 | Fourkas et al. |
| 6,221,057 B1 | | 4/2001 | Schwartz et al. |
| 6,416,499 B2 | | 7/2002 | Paul, Jr. |
| 6,562,049 B1 | | 5/2003 | Norlander et al. |
| 6,610,031 B1 | * | 8/2003 | Chin ........................ 604/167.04 |
| 6,981,966 B2 | * | 1/2006 | Green et al. ............. 604/167.02 |
| 2003/0144670 A1 | | 7/2003 | Pavcnik et al. |
| 2003/0216771 A1 | | 11/2003 | Osypka et al. |
| 2004/0230161 A1 | * | 11/2004 | Zeiner ...................... 604/167.06 |
| 2005/0096605 A1 | * | 5/2005 | Green et al. ................... 604/246 |
| 2005/0171479 A1 | | 8/2005 | Hruska et al. |
| 2006/0135977 A1 | * | 6/2006 | Thompson et al. ........... 606/185 |
| 2006/0229564 A1 | * | 10/2006 | Andersen et al. ........ 604/167.03 |

FOREIGN PATENT DOCUMENTS

| | | |
|---|---|---|
| EP | 0 755 694 A1 | 1/1997 |
| EP | 1 374 942 A1 | 1/2004 |
| WO | WO 99/26682 | 6/1999 |

* cited by examiner

HEMOSTATIC VALVE SYSTEM

BACKGROUND

1. Technical Field

The present invention relates to a valve system for use with a medical device. More particularly, the invention relates to a medical device, such as an introducer, having a hemostatic valve system that allows substantially leak-free passage of a medical interventional device, such as a catheter, through the medical device for insertion into a body vessel.

2. Background Information

Numerous procedures have been developed in modern medicine that require the percutaneous insertion of one or more medical interventional devices into the vascular system. Such procedures include, for example, percutaneous transluminal coronary angioplasty (PTCA), X-ray angiographic procedures, and the like.

The medical interventional devices intended for use in such procedures may be introduced into the vascular system by a variety of known techniques. One widely-used technique is the Seldinger technique. In the Seldinger technique, a surgical opening is made in an artery or vein by a needle, and a wire guide is inserted into the artery or vein through a bore in the needle. The needle is thereafter withdrawn, leaving the wire guide in place. A dilator which is positioned within the lumen of an introducer device is then inserted over the wire guide into the artery or vein. Once the introducer is properly positioned within the artery or vein, the dilator is withdrawn. The introducer may then be utilized in conventional fashion for the insertion therethrough of a variety of types of medical devices, such as catheters, cardiac leads, and the like.

In many cases, an introducer will include one or more hemostatic valve members (also referred to as check valves) for inhibiting leakage of bodily fluids, such as blood, back through the introducer as a medical interventional device is inserted or withdrawn therethrough. The valve members are generally positioned in a housing of the introducer, between a main body portion and an end cap. Typically, such valve members comprise one or more elastomeric disks having one or more slits extending through all or a portion of the disk. On some occasions the valve members may comprise at least one disk having one or more slits, and at least one additional disk having a hole extending through the center of the disk. The slits and/or holes are sized to enable the medical interventional device to pass through the valve member, and to substantially prevent the backflow of fluids through the valve. Hemostatic valves are well known in the medical arts for such purpose, and no further general discussion of the use and function of such valves is necessary to an understanding of the present invention.

Frequently, it is necessary to replace a previously-inserted medical interventional device with another interventional device of a different diameter, or with a different type of device. Such exchanges are normally made over a wire guide, wherein the old device is withdrawn over the wire guide, and the new device is thereafter inserted into the vasculature over the existing wire guide or a newly-inserted wire guide. In many such cases, elastomeric hemostatic valves are provided in an attempt to minimize leakage of blood back through the introducer. Such valves are dependent upon the elasticity of the valve body, and its ability to draw back upon itself to seal any gap created upon insertion or withdrawal of a device through the valve.

Known slitted hemostatic valves generally include one or more slits that criss-cross and span a center portion of the valve, or a hole disposed through the center of the disk. As the interventional device is passed through the center of a slit valve, the slits open outwardly and form one or more generally "V"-shaped openings that are disposed along the outer surface of the interventional device. Such linear-type openings do not form tight seals, and inherently create gaps that permit the leakage of at least some fluid. As a result, hemostatic valve systems often comprise two or three such valve members that are aligned in the valve housing in a manner such that the slit portions are not in axial alignment. Although this arrangement may reduce the amount of leakage compared to the use of a single valve member, the presence of the gaps continues to provide a conduit from which some leakage may occur. Similarly, the various flaps resulting from the slits do not always re-set in the proper manner following passage of the interventional device, thereby creating additional gaps through which fluid may leak.

In addition to the foregoing, when larger slitted valves are utilized, the interventional devices may tear the valve disk beyond the slits upon insertion. This is particularly true when larger size interventional devices are inserted. In such cases, multiple valve disks must be incorporated in order to provide a reasonable degree of confidence that the valve system will continue to provide at least some leakage control. In some cases, the damage to the valve may be so severe, that it may be necessary to incorporate another type of valve, such as a Tuohy-Borst type valve, to the introducer.

Similarly, when smaller slitted valves are utilized, the valves are also subject to tearing when smaller size interventional devices are passed therethrough. Small size interventional devices are often delicate, and possess little hoop strength. When such devices are passed through a small valve member, the thickness and strength of the valve member may cause damage to the delicate structure upon passage therethrough of the interventional device. When small disks are used, the clearance between the opening in the disk and the interventional device can be so slight that it may be difficult to insert and/or withdraw the interventional device. In addition, on some occasions, additional small diameter tubing must be used to keep the valve open so that a catheter may be passed therethrough. When additional equipment is required, such as a small diameter tube or a Tuohy-Borst valve as described, the surgeon's hands, and attention, may be unduly distracted at the very time when all possible focus should be on the major task at hand.

When one or more disks having a hole through the center are used, the disks will only retract back to the size of the center hole following removal of the catheter. As a result, the respective center holes allow leakage once the catheter is removed. Such valves may be satisfactory when there is no need to remove the catheter that seals the opening, however, they are problematic when the catheter is removed and the center opening is created.

It is desired to provide a hemostatic valve system for a medical device that provides an effective seal, and that avoids the problems encountered with prior art seals.

BRIEF SUMMARY

The problems of the prior art are addressed by the present invention. In one form thereof, the invention comprises an introducer for use in inserting an interventional device into a body vessel of a patient. The introducer comprises a housing having a proximal opening, a distal opening, and a chamber disposed therebetween. A sheath, defining a conduit for the interventional device, extends distally from the housing distal opening. A valve system is disposed in the housing chamber. The valve system comprises a plurality of valve members axially arranged in the chamber. Each valve member has a generally circular hole extending therethrough, which holes are sized for passage of the interventional device. Each valve member is aligned in the chamber in a manner such that each of the holes is sequentially penetrable by the interventional device, and such that a hole in one valve member is covered by an adjoining valve member.

In another form thereof, the invention comprises a hemostatic valve system for use in a medical introducer. The valve system comprises a plurality of valve members axially arranged in the medical introducer, and having a hole extending therethrough. The holes have a diameter that does not substantially exceed a diameter of an interventional device to be passed through the medical introducer and the valve members. The valve members are aligned in the medical introducer such that the holes are penetrable by the interventional device, and such that a hole in one valve member is covered by an adjoining valve member.

In still another form thereof, the invention comprises a method of introducing an interventional device to a target site in the vasculature of a patient. An introducer is provided for use in inserting the interventional device. The introducer comprises a housing having a proximal opening, a distal opening, and a chamber disposed therebetween. A sheath extends distally from the housing distal opening, wherein the sheath defines a conduit for the interventional device. A valve system is disposed in the housing chamber, the valve system comprising a plurality of valve members axially arranged in the chamber. Each valve member has a generally circular hole extending therethrough, which hole is sized for passage of the interventional device. The valve members are aligned in the chamber such that each of the holes is penetrable by the interventional device, and such that a hole in one valve member is covered by an adjoining valve member. An opener is inserted through the proximal end of the introducer, and advanced through the introducer in a manner such that the opener sequentially penetrates each of the generally circular holes. A wire guide is inserted through a bore of the opener, and advanced such that it extends through the introducer, and a distal end of the wire guide extends beyond a distal end of the introducer. The opener is withdrawn from the introducer, and the distal end of the wire guide is advanced through a pathway in the vasculature to the target site. The interventional device is introduced over a proximal end of the wire guide, and advanced through the introducer to the target site.

DETAILED DESCRIPTION OF THE DRAWINGS AND THE PRESENTLY PREFERRED EMBODIMENTS

Figure 1:
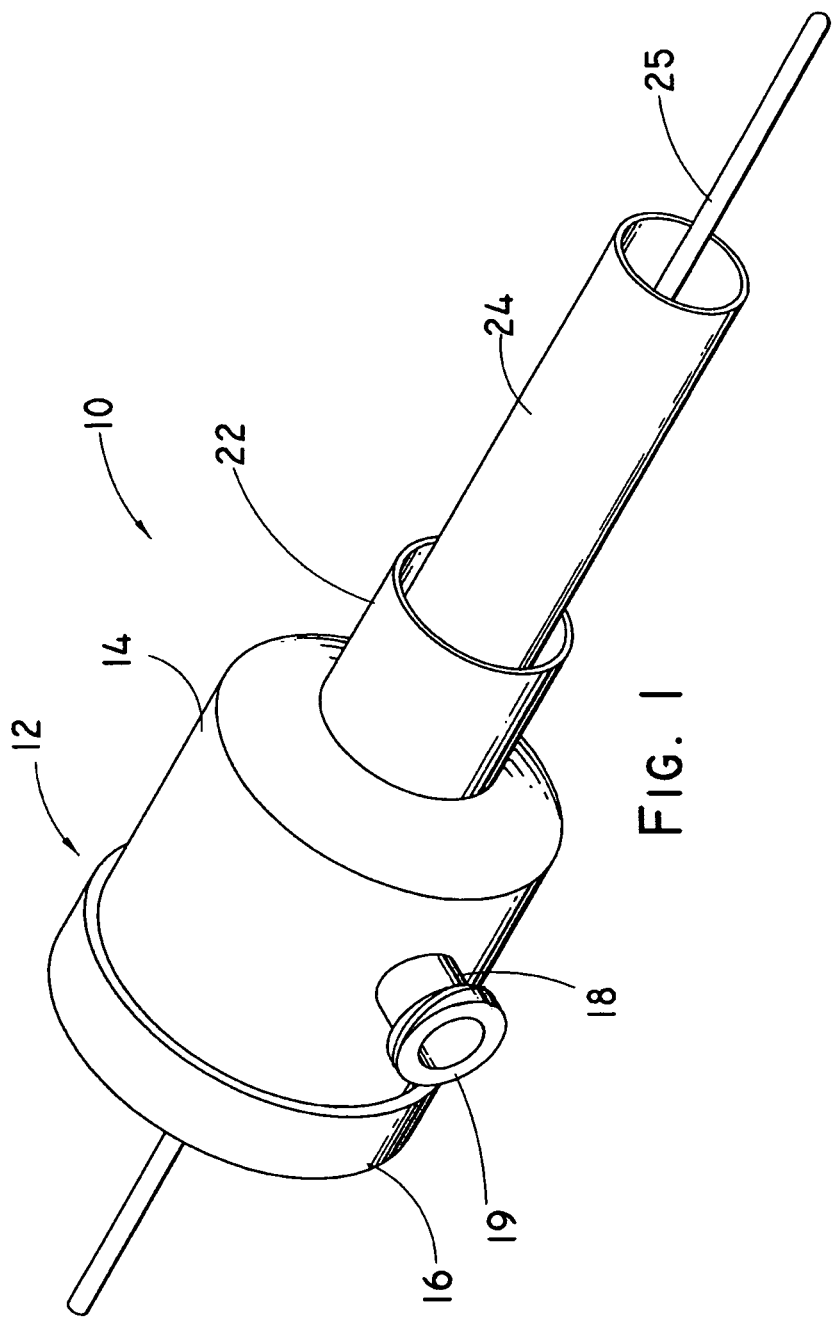
FIG. 1 is a perspective view of one embodiment of a medical introducer apparatus according to the present invention.

For purposes of promoting an understanding of the present invention, reference will now be made to the embodiments illustrated in the drawings, and specific language will be used to describe the same. It is nevertheless to be understood that no limitation of the scope of the invention is thereby intended, the proper scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein.

The present invention relates to a medical introducer apparatus, and to a hemostatic valve system that may be utilized in such an apparatus. In the following discussion, the terms "proximal" and "distal" will be used to describe the opposing axial ends of the apparatus, as well as the axial ends of the valve members and other component features. The term "proximal" is used in its conventional sense to refer to the end of the introducer apparatus (or component thereof) that is closer to the operator during use of the device. The term "distal" is used in its conventional sense to refer to the end of the introducer apparatus (or component thereof) that is initially inserted into the patient, or that is closer to the patient.

Figure 2:
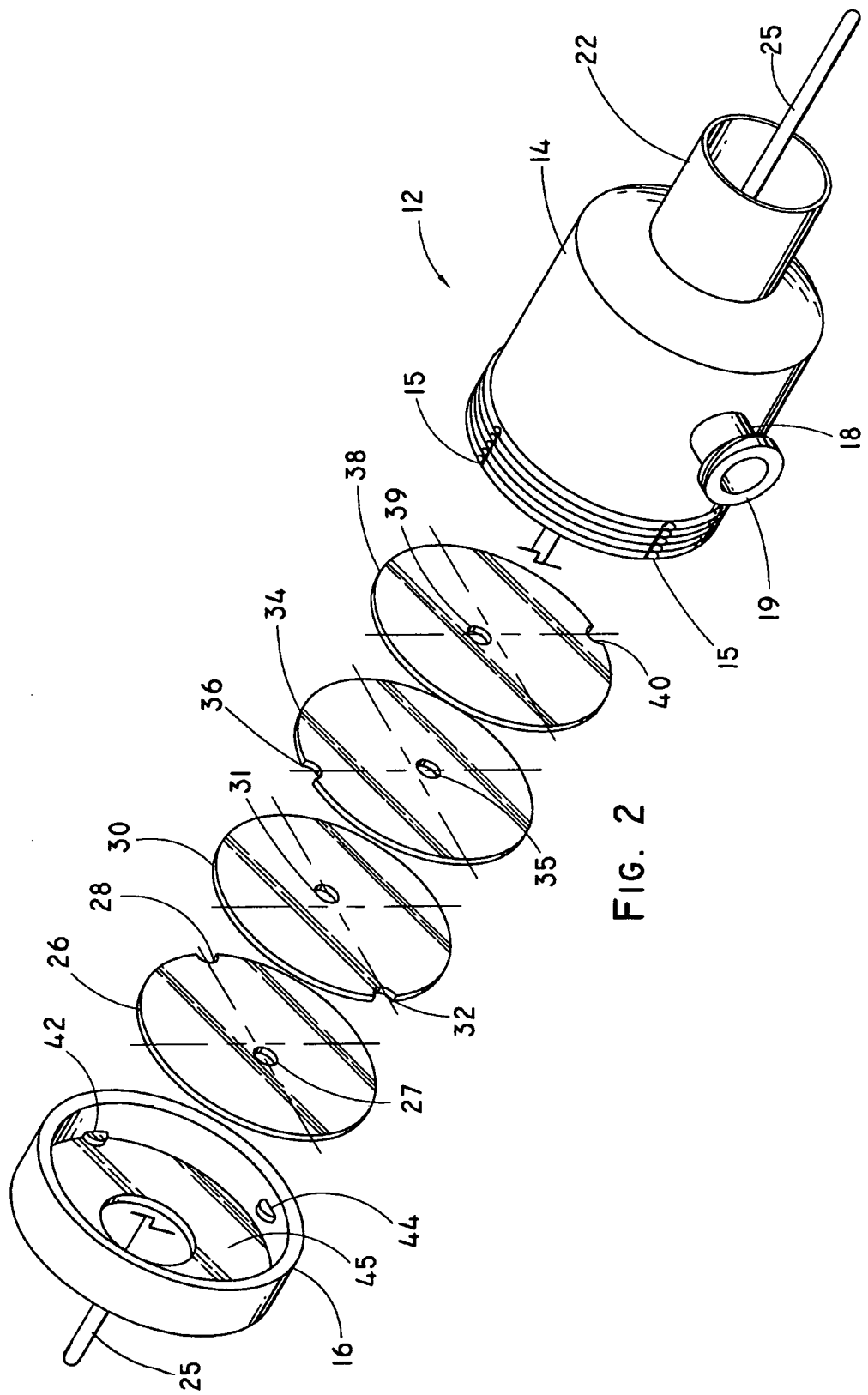
FIG. 2 is an exploded view of a proximal portion of the introducer apparatus of FIG. 1.

FIG. 1 illustrates a perspective view of one embodiment of a medical introducer apparatus 10 according to the present invention. The features of introducer apparatus 10 visible in FIG. 1 are conventional, and are common in many commercially available introducers. FIG. 2 illustrates an exploded view of introducer apparatus 10. The exploded view illustrates one non-limiting example of an inventive valve system for use in the introducer apparatus.

The embodiment of introducer apparatus 10 illustrated herein includes a housing 12, wherein the housing comprises main body 14 and end cap 16. Main body 14 and end cap 16 may be joined in any conventional fashion, such as by a screw fit or a snap fit. In the embodiment shown in FIG. 2, main housing body 14 has one or more screw threads that correspond with a lip or other suitable structure in the end cap. Body 14 also includes a plurality of grooves 15 that generally correspond to tabs in the end cap, as discussed hereafter. Housing 12 may also include a side-arm spout 18 extending in a generally transverse direction from main housing body 14. Preferably, spout 18 includes a lip 19 sized and shaped for threaded or like engagement with a tube or other device (not shown), for use in the transmittal or aspiration of a fluid or a drug in conventional fashion. The distal end of main housing body 14 comprises a smaller diameter portion 22. A removable sheath 24 extends distally from smaller diameter portion 22 of housing 12 in conventional fashion. In the embodiment shown, a wire guide 25 is shown extending through apparatus 10.

The exploded view of FIG. 2 illustrates main housing body 14, end cap 16, and elastomeric valve disks 26, 30, 34, 38 axially aligned between main body 14 and end cap 16. The use of elastomeric disks as hemostatic (check flow) valves is well known in the medical industry. The disks used herein have sufficient elasticity to enable an opening formed therein to stretch to the extent required to allow an interventional device to pass therethrough, and to substantially return to a pre-stretched condition following relaxation of the force generated upon insertion of the device. The disks can be formed to have any desired diameter and thickness, depending upon the size of the interventional device, and the desired pressure rating of the valve system. The disks used herein are preferably formed from elastomeric materials such as silicone or urethane, although any suitable composition known in the art for such purposes may be substituted.

In the preferred embodiment of FIG. 2, each disk has a generally circular hole extending therethrough, which hole is sized to enable passage of the interventional device. Preferably, the hole is capable of being stretched during insertion of an interventional device having a larger diameter than the diameter of the hole, such that there is little or no clearance between the hole and the device so that a tight seal is formed therebetween.

Figure 3:
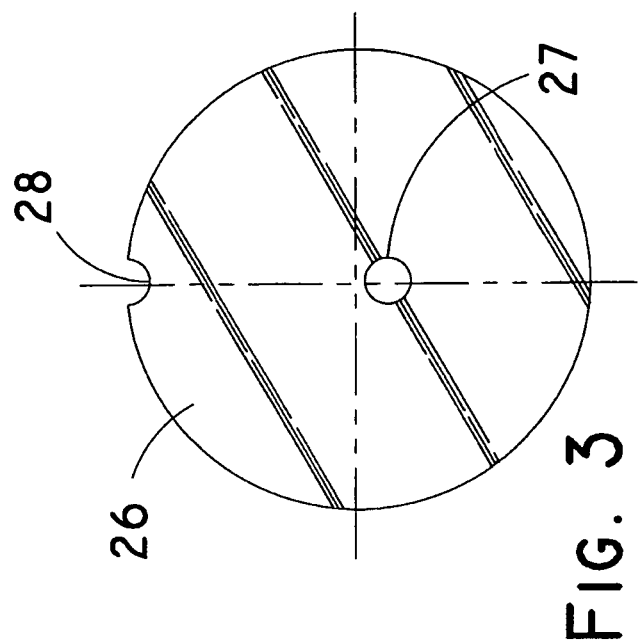
FIG. 3 is a front view of one example of an elastomeric valve disk for use in the present invention.

Disk 26 is shown in FIG. 3 removed from the inventive apparatus to better illustrate features of the disks. Hole 27 is punched or otherwise formed through disk 26. As shown, hole 27 is offset from the radial center of the disk (shown as the intersection of the two axes present as broken lines). The distance of the offset from the center portion of the disk may be selected according to the desired pressure rating for the valve. Preferably, a keyed portion, such as notch 28, is provided along the outer circumference of disk 26, for reasons to be discussed.

In the preferred embodiment shown, apparatus 10 includes multiple disks that are each configured in the same manner as disk 26. As best illustrated in the exploded view of FIG. 2, each disk 26, 30, 34, 38 includes a respective hole 27, 31, 35, 39, and a respective notched portion 28, 32, 36, 40. The holes are offset from the center portion in the manner best shown in FIG. 3. Preferably, the holes are offset in the portion of the disk directly opposite the notched portion.

Figure 4:
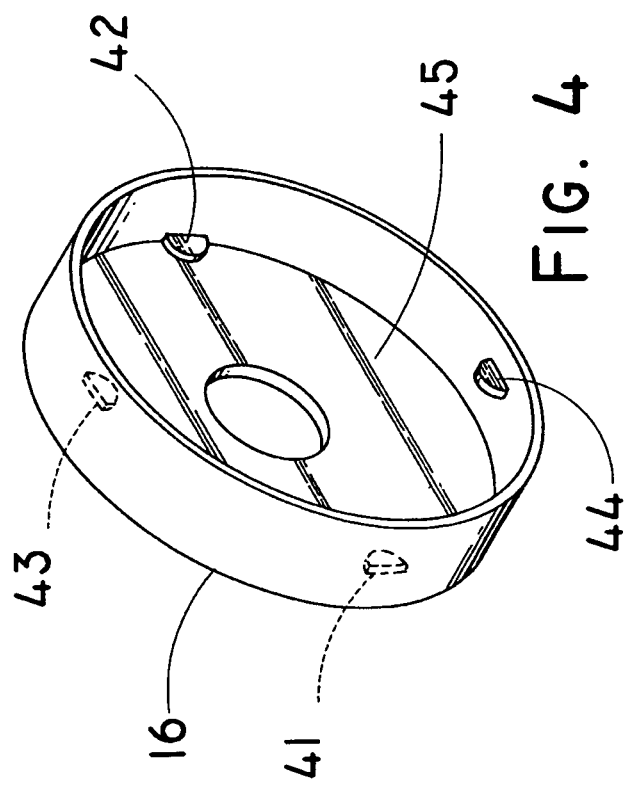
FIG. 4 is a perspective view of an end cap for the apparatus.

The disks and the housing are preferably provided with cooperating structure that maintains the respective disks in a particular orientation within apparatus 10. In the preferred embodiment shown, the disks are each provided with a shaped portion, such as the notched portion 28 shown in FIG. 3. When the apparatus is fully assembled, the shaped portion of the disk cooperates with a corresponding shaped portion, such as a tab, that is provided in the end cap. The shaped portion of the disk and the corresponding shaped portion of the end cap cooperate in the nature of a keyed structure, to maintain the disk in a desired orientation within the housing. FIG. 4 illustrates one possible arrangement of keyed tabs that may be provided on housing end cap 16. In the embodiment shown, housing end cap 16 includes four tabs 41, 42, 43, 44. Tab 42 is the deepest tab in housing end cap 16. When the apparatus is fully assembled, tab 42 corresponds with notch 28 of disk 26, to hold that disk in the preferred rotational orientation. Disk 26 thus essentially rests on floor portion 45 of housing end cap 16. This may also be visualized from the view of FIG. 2. Similarly, tab 41 corresponds with notch 32 of disk 30, tab 43 corresponds with notch 36 of disk 34, and tab 44 corresponds with notch 40 of disk 38. It should be noted that each of the tabs is positioned at a different depth in end cap 16. This depth corresponds to the positioning of the various disks as they are stacked in the housing, and to the position of the notch that corresponds to the respective tab. Each of the tabs thus retains a specified disk in a particular orientation in the housing.

Figure 5:
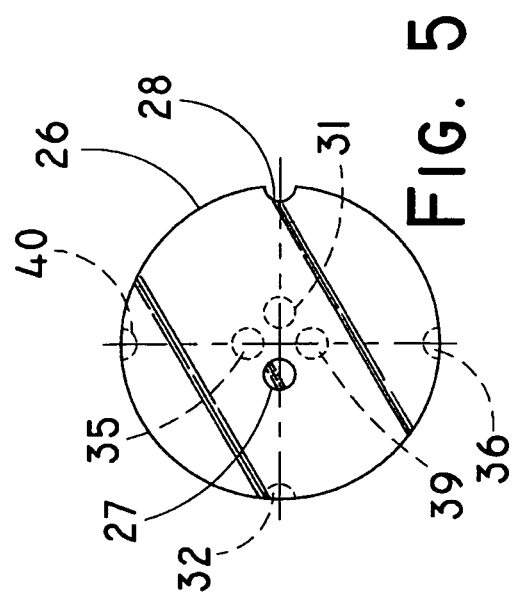
FIG. 5 is a view of one embodiment of a 4-disk valve system of the present invention taken from a proximal perspective.

When the introducer apparatus includes four disks, the disks are preferably aligned as shown in FIG. 2. In this case, disks 26 and 30 are rotated approximately 180 degrees from each other, such that respective notches 28, 32 are disposed 180 degrees apart in the assembled device. Similarly, disks 34 and 38 are rotated so that notches 36, 40 are disposed approximately 180 degrees from each other. Thus, in the finished device, each one of holes 27, 31, 35, 39 is disposed in a separate quadrant of the valve system as shown. Stated another way, in the completed apparatus, there is a hole at 90, 180, 270 and 360 degrees, relative to a designated starting point. This is shown in the disk alignment of FIG. 2, and may also be visualized by the end view of FIG. 5. FIG. 5 comprises the alignment of the disks as they are stacked in the housing, when viewed from a vantage point proximal of disk 26. The features of disk 26, such as hole 27 and notched portion 28, are illustrated in solid lines, since these features are visible in this view. Features of the remaining disks 30, 34, 38, which are successively aligned behind disk 26, are shown in broken lines to indicate the relative positioning of these features relative to the features of disk 26 in the assembled apparatus. As stated, these additional features are not directly visible in the view of FIG. 5 since they are positioned behind disk 26 when viewed from this perspective.

Although FIGS. 2 and 5 illustrate the presence of four disks, the valve system need not include exactly four disks. Thus, more, or fewer, disks may be utilized in a particular case. For example, when the apparatus includes two disks, the disks are preferably aligned such that each disk is rotated about 180 degrees from the other disk. As a result, each one of holes is disposed in a separate circumferential half of the valve system. Similarly, when a valve system includes three disks, the disks may be aligned such that each disk is rotated about 120 degrees from the immediately preceding disk, and each hole is disposed in a separate circumferential third of the valve system. Those skilled in the art will appreciate that other numbers of disks may be used, in which case the disks may be aligned in a corresponding manner.

It is an important feature of the invention to align the disks such that the holes in immediately adjacent disks are not substantially overlapping, and preferably, do not overlap at all. This alignment may be best visualized in FIG. 5. In this arrangement, it is observed that the holes do not overlap when the disks are assembled in the inventive apparatus. Although it is preferred that the holes not overlap, a small amount of overlap may be acceptable in certain instances. Similarly, it is preferred to align the disks such that the holes are equally spaced along the circumference of a valve system, as shown in the embodiment of FIG. 5. However, this is not necessarily required in all instances, as long as the holes in immediately adjacent disks are not substantially overlapping. Nonetheless, it is preferred to align the disks such that the holes are substantially equally spaced, as it is believed that a better seal is provided.

In general, an introducer apparatus having a valve system that includes a large number of valve disks has an increased overall pressure rating when compared to a valve system having a smaller number of disks. For example, the valve system shown in FIGS. 2 and 5 comprising four valves would have a higher overall pressure rating than a valve system having two or three valves, other factors being equal. Similarly, a valve system having disks in which the holes are further away from the radial center of the disk will have a higher pressure rating than a valve system wherein the holes are at or near the radial center of the disk.

Thus, in applications in which valves having a high pressure rating are desired, a valve system having a high number of valve disks (such as four), and/or a valve system wherein the holes in the valve disks are spaced from the center of the disk is preferred. On the other hand, when a low pressure valve system is acceptable, a valve system having a lower number of valve disks (such as two), and/or a valve system wherein the holes in the valve disks are closer to the radial center of the disk may be satisfactory. When utilizing the teachings provided herein, those skilled in the art can readily select a valve arrangement having a desired number of disks, and an appropriate spacing of the hole from the center of the disk, to obtain an appropriate pressure rating for a particular application without undue experimentation.

Figure 6:
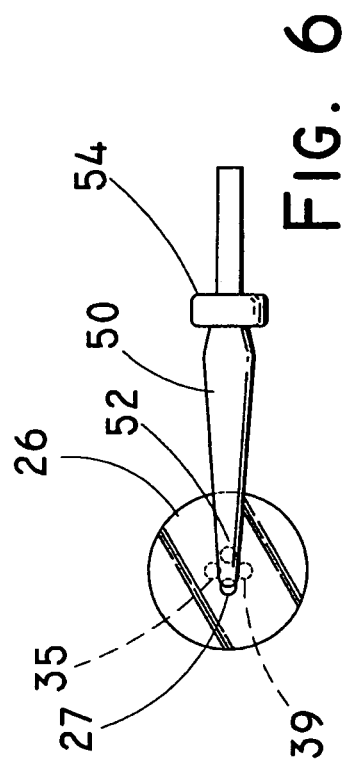
FIG. 6 shows the opener penetrating the hole in the first disk.

The invention may be better explained by the following description of its use. Preferably, an opener is used to initially establish a pathway through the valves of introducer apparatus 10. One embodiment of an opener 50 is illustrated in FIG. 6. Alternatively, the opener may be configured in the manner of a conventional insertion device, such as a J-straightener. FIG. 6 schematically illustrates the arrangement of the disks as disk 26 is initially penetrated by opener 50. In this figure, opener 50 is provided with a narrow tip portion 52 that is initially inserted into apparatus 10. Narrow tip portion 52 is directed in the apparatus such that it initially passes through hole 27 of disk 26. Tip portion 52 is then successively directed through holes 31, 35, 39 of respective disks 30, 34, 38, until it passes through each of the disk valves.

Figure 7:
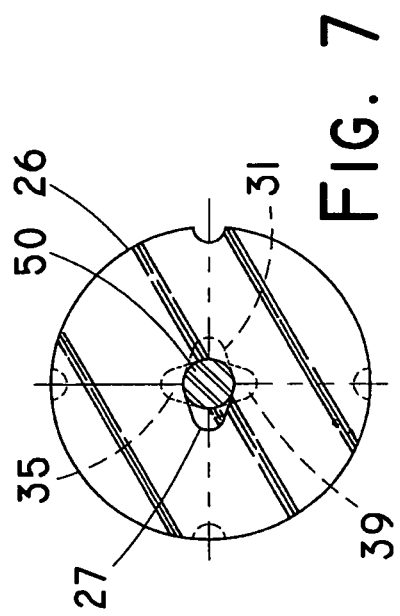
FIG. 7 illustrates the arrangement of disks shown in FIG. 5, following penetration of all four disks by the opener, showing the stretching of the disks toward the radial center of the disk.

Typically, as the opener passes through the successive valve disks, it finds the radially inner edge of each successive hole, at which time the opener can be manipulated to stretch the hole in an up and down, and in a side to side motion. As the tip portion passes through the successive disks, the holes stretch toward the center of the disk. The opener is continually advanced until it reaches the radially inner edge of the next hole, and the stretching process is repeated. This process is continued until the opener has penetrated the hole in each of the successive disks. Once tip portion 52 has passed through all four of the disk holes, the holes are each stretched from the original "rounded" configuration as shown in FIG. 5, to a "stretched" configuration similar to that shown in FIG. 7. In the stretched configuration of FIG. 7, the disks are stretched by the opener in the direction of the radial center of the disk. The void in the radial center of the figure indicates the presence of the opener 50.

If an opener having the configuration of opener 50 is utilized, the opener is preferably inserted until it reaches larger diameter portion 54. If present, large diameter portion 54 acts as a stop to prevent further insertion of the opener. Once the opener has penetrated the disks as shown, a wire guide 25 may be inserted through a central bore of the opener such that is extends axially all the way through apparatus 10. The opener may then be withdrawn leaving the wire guide in position.

Figure 8:
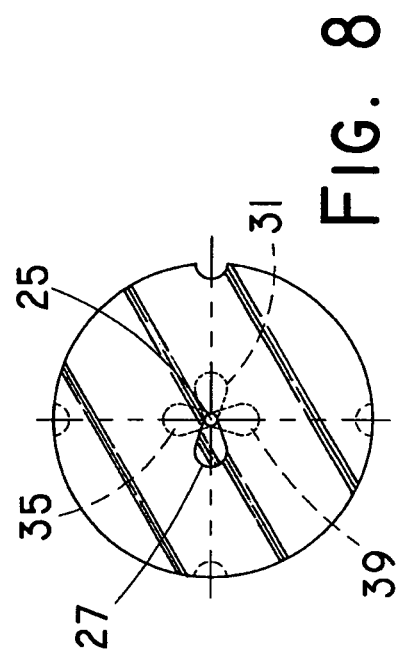
FIG. 8 illustrates the arrangement of disks shown in FIG. 5, following the insertion of a wire guide and the withdrawal of the opener
Figure 10:
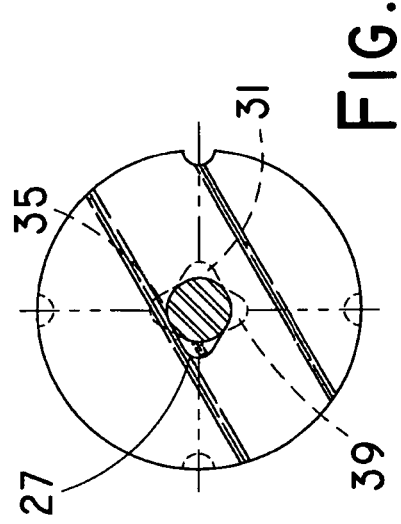
FIGS. 10 and 11 illustrate other stretching patterns of the disks shown in FIG. 8, after the insertion of respective larger interventional devices into the valve system.
Figure 9:
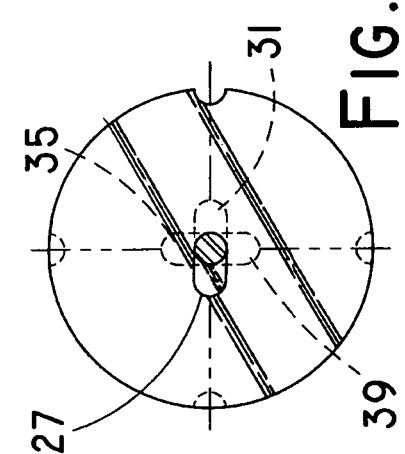
FIG. 9 illustrates the stretching pattern of the disks shown in FIG. 8, after an interventional device has been inserted into the valve system.
Figure 11:
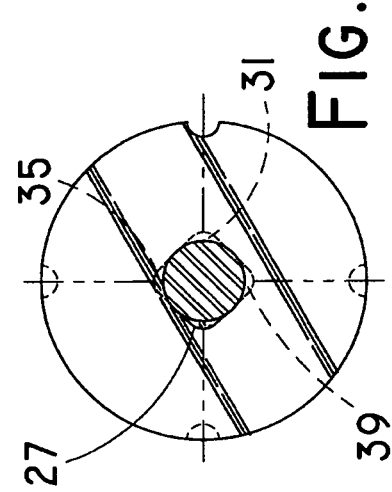

When the opener has been removed and the wire guide is left in position extending through apparatus 10, the holes have a stretched configuration such as that shown in FIG. 8. As shown, the radially inner edge of each successive hole 27, 31, 35, 39, is stretched toward the radial center of the apparatus. At this time, an interventional device, such as a catheter, may be inserted to follow the path through the introducer apparatus established by the wire guide. The hole in each of the elastomeric valve disks will automatically adjust to the dimensions of the inserted device. FIGS. 9, 10 and 11 illustrate examples of the type of stretching of the holes that may be caused by a relatively small diameter (FIG. 9), intermediate diameter (FIG. 10) and large diameter (FIG. 11) interventional device, respectively. In each case, as the tip of the catheter or other interventional device passes through the radial center of the valve system, it stretches the various loops (formed by stretching the respective holes), allowing the catheter to pass through the respective disk. At the same time, the curve of the loops hugs the outer surface of the catheter, thereby maintaining an effective seal therebetween. Once the catheter is removed, the elasticity of the disks causes them to revert to a condition wherein each successive disk covers the hole in an adjoining disk, as best shown in FIG. 5, thereby maintaining the seal.

Disks suitable for use in the present invention may be readily prepared in a manner generally similar to the preparation of existing hemostatic valve disks. In this case, however, rather than forming a slit and/or a central hole through the disk, a hole is punched or otherwise formed through the disk offset from the radial center. Since it is preferred to use disks that are identical to each other (differing only in their alignment in the valve system), a plurality of elastomeric disks may be simply arranged in a stack, and a hole punched through the stack. Similarly, if a notched portion is desired, the notched portion may be also be punched into the stacked disks in a single operation. Those skilled in the art will appreciate that the holes and notched portions may alternatively be formed in the disks by any other conventional method, and all disks need not necessarily have the same orientation with regard to the offset hole and/or notched portion. However, utilizing a plurality of identical disks as described facilitates manufacture of the system.

Although the disks described above include notched portions that serve as "keys" for providing easy alignment of the disks in the housing, any other configuration that is capable of accomplishing the same purpose may be substituted. For example, a flattened portion can be provided along the circumference of the disks, or a slot can simply be cut through the edge of a designated portion of the disk. The housing can be formed to include complementary structure to receive the flattened portion or the slot, once again in the nature of a key. Those skilled in the art will appreciate that other complementary structures may be substituted for those described. Similarly, some disks may be provided with one type of key, such as a notch, while other disks can be provided with another type of key, such as a flattened portion. As still another alternative, the housing can be formed to have any other type of receptacle, tab, or guide that serves to maintain a disk in a constant orientation relative to other disks.

As yet another alternative, it is not required that the disks, or the housing, include a keyed portion at all. In some instances, merely stacking the disks in the housing in a manner similar to that of FIG. 5, wherein each successive disk substantially covers the hole of a preceding disk, will be sufficient. This will generally be true when only a low pressure rating of the valve disks is required.

Figure 12:
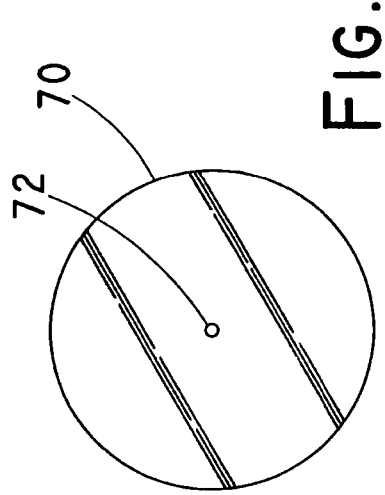
FIG. 12 is an example of a guide disk that may be utilized in connection with the inventive valve system.

As still another alternative, the valve system of the introducer apparatus can additionally include one or more additional disks not having the described configuration, and/or not covering the hole of a preceding disk. In one such embodiment, an additional disk can be provided in the housing body directly proximal of the disks of the described valve system. One such disk 70 is illustrated in FIG. 12. As shown, this disk includes a hole 72 through the radial center of the disk. Although the disk shown in FIG. 12 does not include a notch or other keyed portion, such portion(s) can be included if desired. This additional disk having a central hole may be particularly helpful in configurations where the holes in the aligned disks share a common point, such that the opener or wire guide may travel through the valve system substantially in a straight line. This disk is generally provided to guide the opener or wire guide through the system. As a result, this guide disk (or guide valve) may be arranged in the valve system such that it is the first disk encountered by the wire or device as it enters the proximal end of the introducer apparatus.

Utilizing disks having the offset holes as described for sealing is advantageous when compared to slitted valves. It is generally beneficial to utilize a curved line rather than straight lines in a passage or opening for an interventional device. A curved line has a better ability to "hug" the outer surface of the interventional device than a straight line, and thereby provides a better seal. In addition, the risk of tearing the disk is reduced, due to the larger opening that is possible with a hole when compared to a slitted opening. As a result, less force is required to close possible gaps in the valve system, and the insertion of larger devices is facilitated. Taking advantage of the stretching ability of the elastomeric disks provides the versatility to handle interventional devices having a wide range of diameters, and allows rapid recovery to the closed condition following passage therethrough of the device. Concern about the proper re-seating of the flaps of a V-shaped slitted opening following passage of the device is generally eliminated.

In addition to the foregoing, the stretching ability of the disks enables the sequential introduction and removal of interventional devices of a wide range of diameters through the same valve system. Thus, for example, a small catheter can be introduced and thereafter withdrawn, followed by the introduction of a larger catheter. In either case, the combination of the elasticity of the disks and the use of the circular offset openings provides a very reliable seal. Similarly, with a circular hole, the pressure is distributed in a substantially equal manner around the entire outer circumference of the interventional device. As a result, less pressure is exerted against localized portions of the surface of the interventional device. This is particularly advantageous for the insertion of delicate and/or very small diameter devices, which may be at risk of collapse if excessive pressure is exerted on the device during introduction. Depending upon the composition of the disk, a hole may stretch up to about five times its normal size.

Those skilled in the art will appreciate that lubricants and other conventional additives for use with conventional check flow valves may also be utilized with the valves of the present invention. In particular, the use of lubricants between the disks may be desired to inhibit stickage of adjacent disks, and to assist in the smooth movement of the interventional device through the holes.

It is therefore intended that the foregoing detailed description be regarded as illustrative rather than limiting, and that it be understood that it is the following claims, including all equivalents, that are intended to define the spirit and scope of this invention.

The invention claimed is:

1. An introducer for use in inserting an interventional device into a body vessel of a patient, the introducer comprising:
   a housing, said housing having a proximal opening, a distal opening, an interior housing surface, and a chamber disposed between said proximal opening and said distal opening within said interior housing surface, said interior housing surface including a plurality of tabs axially and circumferentially spaced therealong;
   a valve system disposed in said housing chamber, said valve system comprising a plurality of identical valve members axially arranged in said chamber, each said valve member having a generally circular hole extending therethrough and sized for passage of said interventional device, each said valve member being aligned in said chamber such that each of said holes is penetrable by said interventional device, and such that said hole in one valve member is covered by an adjoining valve member, each said identical valve member comprising a notch disposed along a circumferential edge thereof, said notch positioned along said circumferential edge such that one of said tabs is receivable therein when said valve member is arranged in said chamber;
   a sheath extending distally from the housing distal opening, said sheath defining a conduit for said interventional device;
   said valve members being axially arranged in said chamber such that said holes are substantially non-coaxial and are offset from a center portion of said valve members, said holes further being capable of substantially conforming to a profile of the interventional device passed therethrough; and
   wherein said plurality of identical valve members comprises four valve members, said valve members being aligned in said housing such that each of said holes is disposed in a distinct quadrant of said valve system.

2. The introducer of claim 1, wherein said housing comprises a body portion and an end cap, and wherein said valve system is axially disposed between said body portion and said end cap.

3. The introducer of claim 1, wherein said hole in one valve member is fully covered by an adjoining valve member.

4. The introducer of claim 1, wherein said valve members are substantially round.

5. The introducer of claim 1, wherein said valve members comprise elastomeric disks, further comprising a guide valve in said housing chamber, said guide valve being aligned proximal to said elastomeric valve members of said valve system, said guide valve having a hole disposed substantially in a center of said guide valve for guiding said interventional device to an axial center portion of said valve members.

6. The introducer of claim 1, wherein said tabs are evenly spaced along a circumference of said interior housing surface.

7. The introducer of claim 1, wherein each of said generally circular holes is positioned at a portion of the respective valve member directly opposite from said notch of the respective valve member.

8. A hemostatic valve system for use in a medical introducer, said valve system comprising:
   a plurality of valve members each having a hole extending therethrough, said valve members axially arranged in said medical introducer, said holes having a diameter that does not substantially exceed a diameter of an interventional device to be passed through said medical introducer and said valve members, said valve members being aligned in said medical introducer such that said holes are penetrable by said interventional device, said valve members being axially arranged in said medical introducer such that each of said holes is substantially non-coaxial with reference to other valve member holes, said holes being offset from a center portion of said valve members, and such that said hole in one valve member is covered by an adjoining valve member;
   wherein said valve members are identical, and said holes are capable of substantially conforming to a profile of the interventional device passed therethrough; and
   wherein said plurality of identical valve members comprises four valve members, said valve members being aligned in said medical introducer such that each of said holes is disposed in a separate quadrant of said valve system, wherein said hole in one valve member is fully covered by an adjoining valve member.

9. The valve system of claim 8, wherein said identical valve members comprise elastomeric disks, and wherein each of said identical valve members comprises a key portion, said key portion sized and shaped to engage a corresponding key portion in a body portion of said medical introducer to retain said valve members in an orientation in said medical introducer.

10. The valve system of claim 9, wherein said valve member key portion comprises a notch disposed along a circumferential edge of the respective valve member.

11. The valve system of claim 9, further comprising a guide valve aligned in said medical introducer proximal to said elastomeric valve members, said guide valve having a hole disposed substantially in a center of said guide valve.

12. A hemostatic valve system for use in a medical introducer, the valve system comprising:
a plurality of valve members each having a hole extending therethrough, the valve members axially arranged about an axial center thereof and such that:
a) the hole in each valve member is covered by an adjoining valve member;
b) the hole in each valve member is non-coaxial with respect to the hole in any other valve member, such that the valve members have no common openings with respect to all valve members;
c) the holes of respective valve members are substantially equidistant from the axial center of the valve members; and
d) the hole in each valve member is equally and circumferentially disposed from each adjoining valve member about the axial center, such that a center of each of the holes of said valve members defines a vertex of a regular polygon about said axial center.

13. The valve system of claim 12, wherein said valve members are aligned in said valve system such that a radial pressure asserted by the valve members upon an interventional device arranged for passage through said medical introducer and said valve member holes is proportionally distributed around an axis of the valve system, such that maximum pressure points upon the interventional device form the vertices of the regular polygon about a center axis of the interventional device.

* * * * *